(12) United States Patent
Asaff Torres et al.

(10) Patent No.: US 10,011,509 B2
(45) Date of Patent: Jul. 3, 2018

(54) METHOD AND SYSTEM FOR THE INTEGRAL TREATMENT OF WASTEWATER FROM THE MAIZE INDUSTRY

(71) Applicant: CENTRO DE INVESTIGACIÓN EN ALIMENTACIÓN Y DESARROLLO, A.C., Hermosillo (MX)

(72) Inventors: Ali Jesus Asaff Torres, Hermosillo (MX); Maria Yolanda Reyes Vidal, Hermosillo (MX)

(73) Assignee: CENTRO DE INVESTIGACION EN ALIMENTACION Y DESAROLLO, A.C., Hermosillo, Sonora (MX)

( * ) Notice: Subject to any disclaimer, the term of this patent is extended or adjusted under 35 U.S.C. 154(b) by 0 days.

(21) Appl. No.: 14/765,256

(22) PCT Filed: Jan. 31, 2014

(86) PCT No.: PCT/MX2014/000039
§ 371 (c)(1),
(2) Date: Jul. 31, 2015

(87) PCT Pub. No.: WO2014/119990
PCT Pub. Date: Aug. 7, 2014

(65) Prior Publication Data
US 2015/0368138 A1 Dec. 24, 2015

(30) Foreign Application Priority Data
Feb. 1, 2013 (MX) .................... MX/a/2013/002096

(51) Int. Cl.

| | | |
|---|---|---|
| C02F 9/00 | (2006.01) | |
| C02F 1/44 | (2006.01) | |
| C02F 1/52 | (2006.01) | |
| C02F 1/24 | (2006.01) | |
| C02F 1/38 | (2006.01) | |
| C02F 1/56 | (2006.01) | |
| C02F 1/66 | (2006.01) | |
| C02F 3/34 | (2006.01) | |
| C02F 3/00 | (2006.01) | |
| C07C 51/42 | (2006.01) | |
| C07C 51/487 | (2006.01) | |
| C09K 3/00 | (2006.01) | |
| C02F 3/28 | (2006.01) | |
| C02F 1/00 | (2006.01) | |
| C02F 101/30 | (2006.01) | |
| C02F 101/34 | (2006.01) | |
| C02F 103/32 | (2006.01) | |

(52) U.S. Cl.
CPC ............... *C02F 9/00* (2013.01); *C02F 1/444* (2013.01); *C02F 1/52* (2013.01); *C02F 3/342* (2013.01); *C07C 51/42* (2013.01); *C07C 51/487* (2013.01); *C09K 3/00* (2013.01); *C02F 1/24* (2013.01); *C02F 1/385* (2013.01); *C02F 1/441* (2013.01); *C02F 1/442* (2013.01); *C02F 1/5263* (2013.01); *C02F 1/56* (2013.01); *C02F 1/66* (2013.01); *C02F 3/28* (2013.01); *C02F 2001/007* (2013.01); *C02F 2101/30* (2013.01); *C02F 2101/345* (2013.01); *C02F 2103/32* (2013.01); *C02F 2301/106* (2013.01)

(58) Field of Classification Search
None
See application file for complete search history.

(56) References Cited

U.S. PATENT DOCUMENTS

| | | |
|---|---|---|
| 5,425,956 A | 6/1995 | Shahidi et al. |
| 5,443,852 A | 8/1995 | Shahidi et al. |
| 5,637,618 A | 6/1997 | Kurtz et al. |

(Continued)

FOREIGN PATENT DOCUMENTS

| | | |
|---|---|---|
| CN | 103349258 | 10/2013 |
| EP | 0883999 | 12/1998 |

(Continued)

OTHER PUBLICATIONS

International Search Report for PCT/MX2014/000039, English Translation attached to original, Both completed by the Spanish Patent Office dated Sep. 23, 2014, All together 9 Pages.
Valderrama-Bravo et al. Journal of Food Engineering 2012, vol. 110, No. 3, pp. 478-486, "Constant pressure iltration of lime water nejayote used to cook kernels in maize processing".
Rosentrater, Waste Management 2006, vol. 26, pp. 284-292, "A Review of corn masa processing residues, Generation, properties, and potential utilization".
Valderrama-Bravo et al. CyTA Journal of Food May 20, 2013, vol. 11, pp. 75-83, "Physico-mechanic treatment of nixtamalization by-product nejayote".

(Continued)

*Primary Examiner* — Renee Claytor
*Assistant Examiner* — Sharon M. Papciak
(74) *Attorney, Agent, or Firm* — Brooks Kushman P.C.

(57) ABSTRACT

A process for the treatment of wastewater, commonly known as nejayote, from the nixtamal, masa and tortilla industry, having an improved method for removing the insoluble fraction and a filtration system for separating and concentrating the fractions forming the nejayote is described. The method includes the steps of: (a) neutralizing the nejayote; (b) enzymatically hydrolyzing the starch granules; and (c) flocculating and separating the insoluble fraction. The system includes the steps of (a) microfiltration; (b) ultrafiltration for concentrating long-chain carbohydrates; (c) ultra/nano filtration for concentrating medium-size compounds; and (d) nanofiltration/reverse osmosis for concentrating small molecules and obtaining water of sufficient quality that it can be re-used or safely discharged into the environment. In one embodiment of the invention, in order to remove unwanted phenolic compounds, the process includes a method including the steps of: (a) acidifying the effluents at pH<4; and (b) flocculating and separating the unwanted insoluble fraction.

21 Claims, 2 Drawing Sheets

(56) References Cited

U.S. PATENT DOCUMENTS

| | | |
|---|---|---|
| 5,707,524 A | 1/1998 | Potter et al. |
| 5,866,608 A | 2/1999 | Kurtz et al. |
| 5,883,086 A | 3/1999 | Craft |
| 6,099,854 A | 8/2000 | Howard et al. |
| 6,150,408 A | 11/2000 | Nair et al. |
| 6,261,565 B1 | 7/2001 | Empie et al. |
| 6,310,100 B1 | 10/2001 | Suzuki et al. |
| 6,313,171 B1 | 11/2001 | Bok et al. |
| 6,368,833 B1 | 4/2002 | Borneman et al. |
| 6,828,136 B2 | 12/2004 | Borneman et al. |
| 7,323,511 B2 | 1/2008 | Cholli et al. |
| 7,736,509 B2 | 6/2010 | Kruse |
| 7,851,005 B2 | 12/2010 | Bingley et al. |
| 8,709,526 B2 | 4/2014 | Wolf et al. |
| 8,741,376 B2 | 6/2014 | Broekaert et al. |
| 2005/0238789 A1 | 10/2005 | Cholli et al. |
| 2006/0110520 A1 | 5/2006 | Midorikawa et al. |
| 2006/0286202 A1 | 12/2006 | Boghani et al. |
| 2006/0286203 A1 | 12/2006 | Boghani et al. |
| 2006/0286259 A1 | 12/2006 | Hargreaves |
| 2007/0059344 A1 | 3/2007 | Wolf et al. |
| 2007/0190209 A1 | 8/2007 | Sinnott |
| 2007/0264401 A1 | 11/2007 | Taormina et al. |
| 2007/0292539 A1 | 12/2007 | Vorsa et al. |
| 2007/0292540 A1 | 12/2007 | Gow et al. |
| 2008/0210632 A1 | 9/2008 | Kruse |
| 2008/0227832 A1 | 9/2008 | Oka et al. |
| 2008/0248161 A1 | 10/2008 | Inakufu et al. |
| 2009/0011078 A1 | 1/2009 | Johnson |
| 2009/0038023 A1 | 2/2009 | Weiner et al. |
| 2010/0062131 A1 | 3/2010 | Gouka et al. |
| 2010/0112133 A1 | 5/2010 | Mech |
| 2010/0311828 A1 | 12/2010 | Borochov-Neori et al. |
| 2011/0014279 A1 | 1/2011 | Mora-Gutierrez et al. |
| 2011/0020498 A1 | 1/2011 | Broekaert et al. |
| 2011/0027433 A1 | 2/2011 | Ruf et al. |
| 2011/0064778 A1 | 3/2011 | Moser et al. |
| 2011/0229625 A1 | 9/2011 | Hiatt et al. |
| 2011/0236560 A1 | 9/2011 | Perlman |
| 2011/0244073 A1 | 10/2011 | Broekaert et al. |
| 2012/0047600 A1 | 2/2012 | Zhou |
| 2012/0202778 A1 | 8/2012 | De Lorgeril et al. |
| 2012/0220662 A1 | 8/2012 | Gonzalez Perez et al. |
| 2012/0264832 A1 | 10/2012 | Gurin |
| 2013/0041036 A1 | 2/2013 | Rios et al. |
| 2013/0177506 A1 | 7/2013 | Atkins et al. |
| 2013/0280401 A1 | 10/2013 | Degenhardt et al. |
| 2013/0296613 A1 | 11/2013 | Kishi et al. |
| 2013/0323353 A1 | 12/2013 | Koppe et al. |
| 2014/0010921 A1 | 1/2014 | Mech |
| 2014/0072672 A1 | 3/2014 | Nisbet et al. |
| 2014/0106047 A1 | 4/2014 | Gurin et al. |
| 2014/0148488 A1 | 5/2014 | Zemel et al. |

FOREIGN PATENT DOCUMENTS

| | | |
|---|---|---|
| MX | 53557 | 4/1953 |
| MX | 5005 | 2/1983 |
| MX | 189541 | 3/1994 |
| MX | YU03000005 | 5/2005 |
| MX | PA04012744 | 6/2006 |
| MX | PA05012804 | 6/2006 |
| MX | PA05011797 | 9/2006 |
| MX | PA05008124 | 1/2007 |
| MX | 2007010310 | 3/2009 |
| MX | 2009008890 | 10/2009 |
| MX | 2012007621 | 12/2013 |
| MX | 2013000943 | 5/2015 |
| WO | 2004023892 | 3/2004 |
| WO | 2004110975 | 12/2004 |
| WO | 2009143416 | 11/2009 |
| WO | 2011021066 | 2/2011 |

OTHER PUBLICATIONS

Ramirez-Romero et al. Revista Mexicana de Ingenieria Quimica Dec. 2013, vol. 12, No. 3, pp. 463-471, English Abstract attached to original document, "Study of Nejayote as Culture Medium for Probiotics and Production of Bacteriocins".

Velasco-Martinez et al. Poultry Science Nov. 1997, vol. 76, No. 11, pp. 1531-1534, "Metabolism and Nutrition, Effect of Dried Solids of Nejayote on Broiler Growth".

Sanchez-Gonzales et al. Letters in Applied Microbiology 2011, vol. 52, pp. 413-419, "Isolation and characterization of new facultative alkaliphilic Bacillus flexus strains from maize processing waste water nejayote".

Website http://www.biobran.org/overview/ Dated Jun. 8, 2012, Retrieved from the Wayback Machine on Apr. 12, 2016, All together 6 Pages. "Biobran MGN-3—An Overview, General non-technical overview of Biobran MGN-3 and its benefits".

METHOD AND SYSTEM FOR THE INTEGRAL TREATMENT OF WASTEWATER FROM THE MAIZE INDUSTRY

CROSS-REFERENCE TO RELATED APPLICATION

This application is the U.S. national phase of PCT Application No. PCT/MX2014/000039 filed on Jan. 31, 2014, which claims priority to MX Patent Application No. MX/a/2013/002096 filed on Feb. 1, 2013, the disclosures of which are incorporated in their entirety by reference herein.

TECHNICAL FIELD OF THE INVENTION

The invention involves an integral process for the treatment of residual water, commonly known as "nejayote", that results from a process called nixtamalization. More particularly, the invention refers to a method to efficiently isolate suspended solid particles and a filtration system to fractionate and concentrate the soluble components present in these effluents so that they can be used in different areas, up to the final endpoint to obtain water with enough quality to be reused or discharged environmentally safely.

BACKGROUND OF THE INVENTION

Nixtamalization is an age-old process that consists of cooking corn grain in alkaline water. The cooked grain is then ground and the product known as "mass" is used to make tortilla, an elemental component of the Mesoamerican peoples' diet and which use has been extended throughout the world. In an industrial scale, the mass is dried and ground, and is commercialized as "nixtamalized" corn flour. In any case, both the water used for the alkaline cooking and the water used for washing the cooked grains, are known as nejayote: an effluent rich in organic matter, composed by both suspended solid particles and solids in solution. Unlike the water used to soak the corn generated by the starch industry, nejayote's composition is highly complex, since it contains the resulting products of the alkaline hydrolysis of the pericarp and part of the endosperm of the grain.

The relationship, composition and nature of the components of nejayote formed or released during nixtamalization depend on several different process parameters, including the variety of the corn grain, hardness of the endosperm, quality and integrity of the grain itself and concentration of the lime (Rosentrater, 2006, Waste Management 26, 284-292), as well as temperature and time of cooking and soaking. In the same review, 12 reports are mentioned in which a range of weight loss during nixtamalization can be established between 0.5 and 14.5% of dry weight, which would mean a range between 2500 mg to 50000 mg of total solid components per liter of nejayote. Of these, suspended solid particles range from 2350 to 5500 mg/L and the rest is soluble material formed by carbohydrates of different chain length, phenolic components and calcium salts. The high concentrations and complexity of the organic material, high pH and temperature make nejayote a highly contaminant effluent and hard to treat by conventional methods.

For example, the compact plants for the treatment of residual water have had little success due to the fact that the presence of elements that inhibit microbial growth in nejayote, and its high organic burden, increase greatly the hydraulic residence times and present inlay problems because of the high contents of calcium. Furthermore, although oxidation lakes are a technically viable option, in the majority of cases the big nixtamal-processing companies and medium-sized and small-sized mills are usually in urban centers. This location does not allow the installation and commissioning of the lakes because of lack of space and bad odor, which would upset the residents of the surrounding areas. Other strategies to make use of this effluent (as described by Viniegra and Ramirez, 2007, MX/A/2007/010310), consist on isolating the suspended solid components of nejayote and reincorporating them to the corn mass with the further addition of the liquid to the nixtamalization process. This, however, results in the final product with unpleasant taste and smell, which are not accepted by the consumer; so this strategy has had little success in its application. In laboratory studies that we have conducted, we have found out that the unwanted organoleptic properties of smell and taste are mainly originated from the phenolic compounds found in nejayote, at pH and temperature of nixtamalization. For example, it was found that a phenolic compound known as ferulic acid is transformed in 4-vinyl-guaiacol, and that orto-oxidative coupling reactions of phenols are promoted. Due to the absence of efficient technologies for the treatment of nejayote, different strategies have directed the efforts to the development of alternate technologies to the traditional nixtamalization process with the purpose of reducing or completely eliminating the generation of nejayote (Wilkinson y Short, 1998, EP0883999; Sánchez y de la Cámara, 2004, WO/2004/023892, 2004; Figueroa y col., 2006, MX/A/2005/011797; Bejarano y col., 2009, WO/2009/143416). Nevertheless, said technologies have been unattractive to be applied due to their high operation and investment costs.

Recently, Asaff et al., 2013 (MX/a/2013/000943) developed a unique technology to eliminate any particles or suspended solids from nejayote, process in which one of its applications would allow the integral treatment of nejayote with the use of membrane technology, an increasingly common technology for the treatment of residual water and other diverse industrial processes. For example in Potter's patent, U.S. Pat. No. 5,707,524, a process and a system for the treatment of residual water is described, for different carbohydrate-containing industries as a fermentable material for yeast production. In the patent, the use of ultra-filtration membranes to concentrate fermentable material and generate water to be reused or discarded to the sewage system with a minimal quantity of contaminants is described. However, recent studies that we have been conducting show that in both cases a series of limiting factors exist, which would prevent their industrial application at reasonable costs. In the first case of elimination of suspended solids, the technology described states that it is necessary to use phosphoric acid or a mixture of phosphoric acid or any of its salts with another strong acid to lower the pH to a range of 4 to 6.5, the optimum range of action of certain kind of enzymes, and on the other hand to give the ionic strength to favor the flocculation of the suspended material. The use of phosphoric acid or any of its salts causes the formation of a buffer solution that requires an increased use of acids to achieve the desired pH. Phosphoric acid, comparatively to other strong inorganic acids, has the highest price in the market, which added to the greater use of acid, increases the cost of operation. On the second case, which uses ultrafiltration membranes, our studies showed that nejayote contains some components that gradually get adsorbed onto the membrane material, causing, after some time of use, pore saturation and obstruction, as well as deterioration due to chemical reactions of positively charged compounds and the material of the membrane. Thus, usage of any kind of membrane, be it ultrafiltration, nanofiltration or reverse osmosis, in the treatment of nejayote obtained or conditioned in the parameters described in the application MX/a/2013/000943, is not technically feasible.

Some other described technologies claim to solve the problem indirectly through the recovery of the products of high value contained in it, like feruladed pentosans or feluric acid, with which its total organic matter decreases. Carvajal-Millan et al., 2005, MX 278768 describe a process of ferulated pentosans that consists of adding etanol to a solid-free nejayote and adjusting the pH to 5, with the intention of precipitating medium and long chain carbohydrates. However, its application on industrial systems is very limited because of the costs involved in the recovery of alcohol, which has a ration of at least 2 to 1 when compared to nejayote. Furthermore, the recovered final product is heterogeneous because it contains carbohydrates of different length as well as starch, and the recovery cost is high because of the quantity of alcohol needed. On the other hand, in the patent of Asaff et al. 2005, MX 278768, they describe a process for the recovery of ferulic acid from nejayote by means of adsorption/desorption processes. That system allows us to keep the phenolic fraction and leave the major organic fraction in solution, composed of carbohydrates of different nature. In both patents, the material successfully removed varies between 5 and 20%, so for the most part, the problem of nejayote is still latent.

Since there are no viable alternatives for the treatment or handling of nejayote to this day, in most cases this effluent is discarded in the municipal sewage, or natural water currents with little to no treatment. This means that the activity of the industry of nixtamal, mass and tortilla has a negative impact in the environment, leaving it vulnerable to fines before environmental regulations get more and more strict. For this reason, it is urgent to generate effective alternatives for the integral treatment of nejayote, facilitating its reuse or discharge in an environmentally safe way; and thus promoting the establishment of socially responsible companies, which have policies of care and conservation of the environment.

SUMMARY OF THE INVENTION

Given what has been previously described and with the purpose of providing a solution to the limiting conditions found, the general objective of the invention is to provide a method and a system, both unique, innovating and efficient, for the integral treatment of the effluents of the corn industry, known as nejayote, that have a direct application as a finishing step of the processes of the nixtamal, nixtamalized corn flour and the tortilla industries.

It is a specific objective of the invention to provide a unique method which is innovative and efficient for the conditioning of nejayote with the purpose of obtaining a product free of suspended solids, ideal to be used in processes that pretend to recover compounds with commercial or strategic value present in residual water.

It is another specific objective of the invention to provide nejayote free of suspended solids in conditions that allow its treatment through physical methods of filtration, particularly ultrafiltration, nanofiltration or reverse osmosis, with the object of using the permeate as process water, or to discharge it to the sewage or natural watercourses in an environmentally safe way.

It is another specific objective of the invention to fractionate and concentrate, according to their molecular weight, compounds with high value present in nejayote, like pentosans and ferulated pentosans, phenolic acids, particularly feluric acid, their dimers, trimers, their glycosilated esters, p-coumaric acid and 4-vinil guaiacol, among others.

It is another specific objective of the invention to fractionate and concentrate, according their effective molecular weight, carbohydrates of different nature and chain length, their monomers, dimers or base trimers, like glucose, xylose, arabinose and galactose, among others, with the purpose of using them in different fields, for example in the production of bioethanol.

It is another specific objective of the invention to isolate via precipitation or filtration or centrifugation dimers, trimers, some esters of ferulic acid and/or coumaric acid, that become insoluble with variations of the pH depending on their pKa and using appropriate flocculants, with the purpose of generating an ideal product for the recovery of compounds of high value like ferulic acid.

One of the preferred modalities of the invention, which includes at least some of the objectives previously stated, involves a method that allows the removal of the suspended solid particles of nejayote, lowering its pH to a value close to neutrality, adding an amylase-type enzyme adequate to the working pH and a flocculant to favor the isolation of the suspended solids. The supernatant free of suspended solids is then fed to a system formed by ultrafiltration and nanofiltration membranes of different effective cut, where the components get fractionated and concentrated according to their molecular weight. Through each step, the effluents lower their organic burden up to the point in which an effluent or permeate is obtained, that can be reused in the nixtamalization or discharged to the sewage or natural watercourses in an environmentally safe way. In addition to the treated water, as a principal product, at least three concentrated fractions are obtained. The first one is rich in content of ferulated pentosans, the second one in dextrins, xylose and arabinose oligomers and glycosylated esters of phenolic compounds; and the third one in monomers, dimers and trimers of sugars and phenolic compounds like ferulic acid, its dimers and trimers.

BRIEF DESCRIPTION OF FIGURES

The details of the invention are described in the following paragraphs along with the figures that accompany them, with the purpose of defining the invention but not to limit it.

DETAILED DESCRIPTION OF THE INVENTION

The present invention comprehends a unique, innovative and efficient method and system which have as objective the integral treatment of effluent of an industry of corn, known as nejayote, and that have a direct application as a finishing step of the processes of the nixtamal, nixtamalized corn flour and tortilla industries. The method is referred to the conditioning of nejayote, that consists in the removal of all the suspended solid particles contained in it, followed by the treatment of the effluent free of said solid particles in a membrane filtration system. In that system the soluble components are fractionated and concentrated according to their molecular weight until the obtention of water as a final permeate, with enough quality to be reused in the nixtamalization process or discharged environmentally safely.

Figure 1:
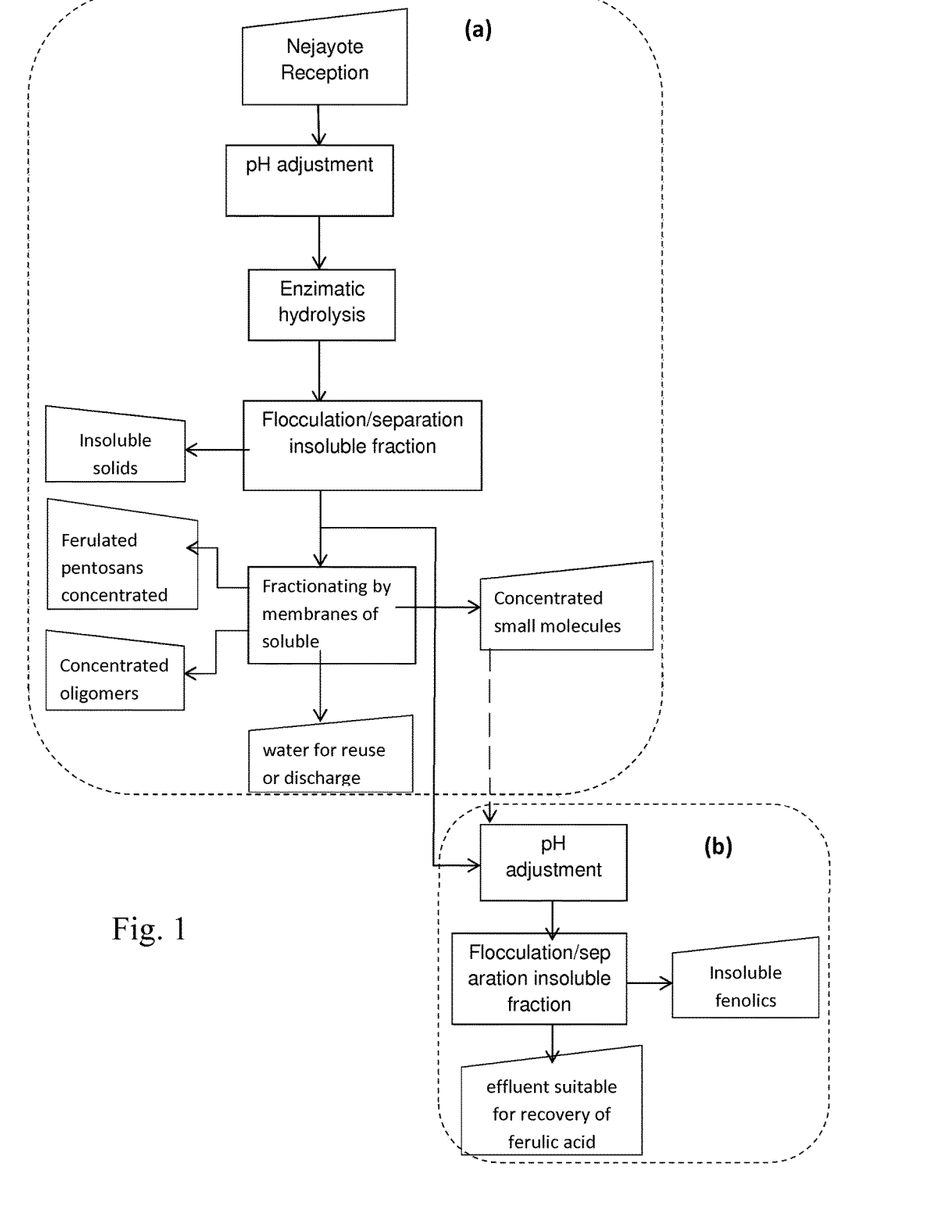
FIG. 1 shows a schematic diagram of the method of the invention to remove (a) the suspended solids of nejayote, isolate and concentrate the soluble compounds up to the obtention of water to be reused or discharged environmentally safely; (b) unwanted phenolic compounds in the processes of recovery and purification of ferulic acid.
Figure 2:
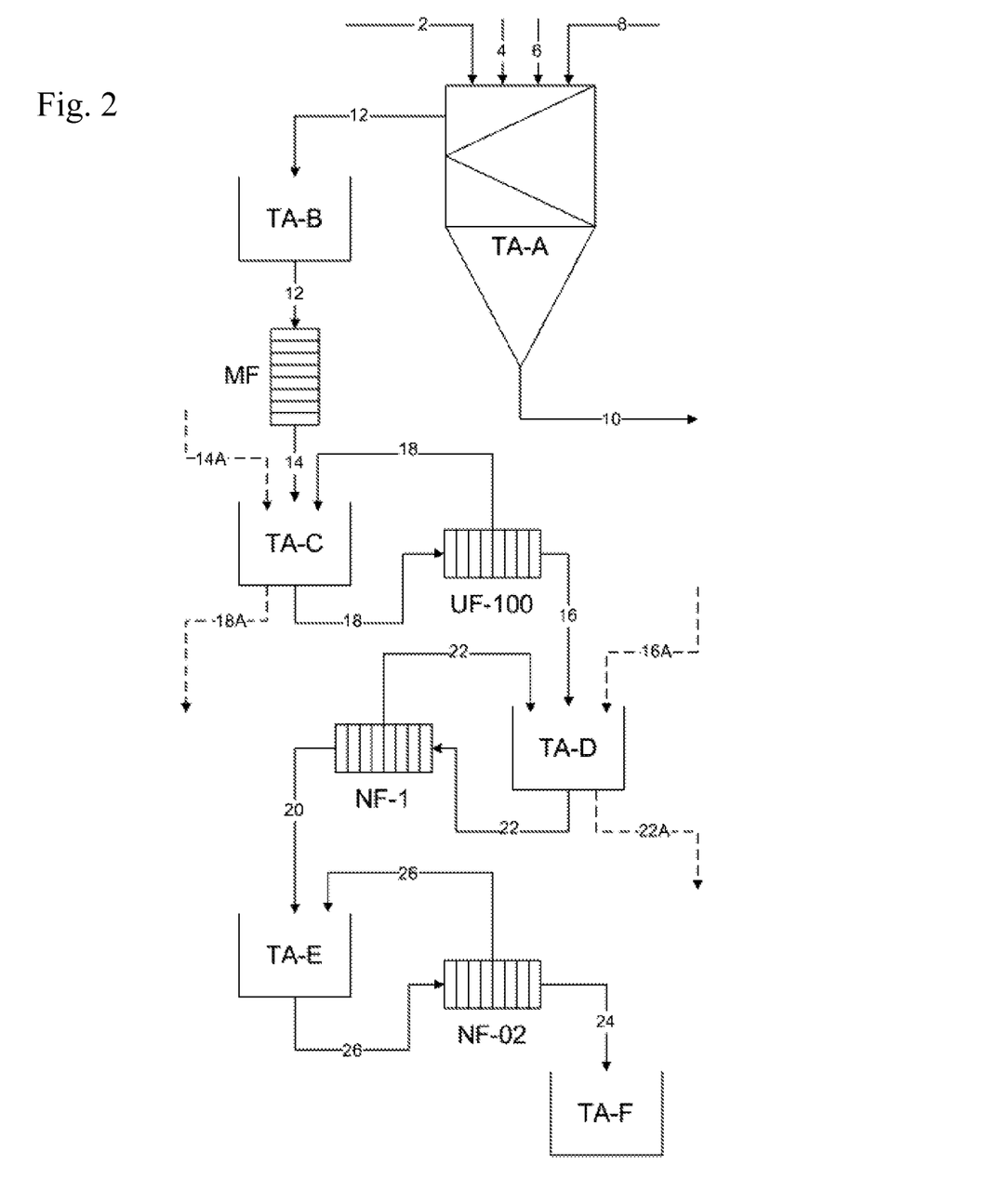
FIG. 2 shows a flow diagram describing the steps and their sequency of the integral process of the present invention for the treatment of nejayote.

One of the preferred modalities of the method is described in reference to FIG. 2, which comprehends a semicontinuous method in which at least two conical vessels with mechanical or pneumatic stirring are used, with alternating operations for the reception and storage of nejayote, its neutralization, enzymatic hydrolysis, flocculation and sedimentation. As a first step, current 2 resulting from the process of nixtamalization, usually with a pH value of between 9 and 12 and a temperature between 70° C. and 90° C. is received and storage in the tank TA-A and is mixed or added to current 4 which contains some acidic substance, preferably sulfuric acid, phosphoric acid, citric acid or $CO_2$. The addition of the acid is done with the purpose of adjusting the pH to a value between 6.5 and 8.0, preferably between 7.0 and 7.5. As second step, the neutralized product from the last step is mixed or added to current 6, containing selected enzymes from the amylase group, preferably amylases of bacterial origin, with an optimum activity between pH values of 6 to 8 and temperatures between 70° C. to 100° C. The volume of the added enzyme oscillates between 10 to 200 µL for each litter of nejayote and it marks the function of the specific activity of the commercial enzyme(s), the content of the material to be hydrolyzed in nejayote and/or the desired time of hydrolysis, which in continuous systems corresponds to the hydraulic residence time. As a third step, the resulting mixture of the second step is incubated during a period between 1 and 60 minutes, preferably between 10 and 30 minutes to provoke the enzymatic hydrolysis of the suspended starchy material present in nejayote, period during which the temperature of the mixture decreases. As described in the application MX/a/2013/000943, these particles are too small to be isolated by physical methods at an industrial scale, but big enough to clot any filtrating surface. For their relevance to the invention, the second and third steps are considered crucial to attain the desired clarification effect. As a fourth step, the hydrolyzed product that comes from the third step is mixed or added to current 8, which has an adequate flocculant, preferably an anionic or cationic flocculant like polyacrylamide or its copolimers or clay containing minerals of the phyllosilicates group or the smectite family with other ingredients. Regarding the cationic flocculants, the optimum quantity needed to obtain an effective flocculation is from 5 to 100 ppm, preferably from 15 to 50 ppm, added from a concentrated solution under stirring, until the obtention of a homogeneous mixture. Regarding the mixture of clay with other ingredients, the optimum quantity is from 200 to 2000 ppm, preferably from 300 to 700 ppm, added as powder and keeping the stirring for 1 to 15 minutes, preferably from 3 to 10 minutes until obtaining the flocculation of the remaining suspended material. The fifth and last step of the method of the present invention consists in the elimination of the flocculated material. The separation of the flocculated fraction of the supernatant lacking any suspended solid particles can be achieved by simple sedimentation or decantation, centrifugation, filtration, flotation or a combination of any of these unit operations. The isolation of the flocculated material gives place to two currents, which in FIG. 2 are represented by currents 10 and 12 respectively. Current 10 contains the insoluble flocculated solid particles, which, unlike the ones obtained by the method described in the application MX/a/2013/000943, are very dense, and hence the floc is compact.

Current 12 contains the soluble compounds and a small quantity of suspended material that could not be removed, usually less than 50 ppm, which is sent to the storage and feed vessel TA-B. During this procedure, the nejayote, with an initial content that can go from 10000 to 20000 ppm and a chemical oxygen demand (COD) of between 8000 to 18000 mg $O_2$/L, has these values lowered between 10 and 15% which corresponds to the recently removed suspended solid particles. This way, the resultant current 12 contains between 8000 to 17000 ppm of soluble solid particles and a COD of between 7000 and 18000 mg $O_2$/L. The flocculated fraction or current 10 is a residue that is usually arranged in sanitary fillings or used for animal feed. Due to its composition this is a fraction that can also be hydrolyzed either chemically or enzymatically, and its sugars can be used for the production of bioethanol, unicellular proteins or in some other biotechnological processes.

The new method to remove suspended solid particles of nejayote, object of the present invention, lays out inventive differences and considerable advantages when compared to the method described in application MX/a/2013/000943. First, in that application, pH of nejayote is adjusted to values between 4.0 and 6.5, preferably between 5.0 and 6.0, with the addition of phosphoric acid and any of its salts, either alone or as a mixture with other strong inorganic acids like sulphuric acid. Addition of phosphoric acid according to its authors, apart from lowering the pH value, it is used to increase the ionic strength of the media with the purpose of promoting a good flocs formation, since the addition of sulphuric acid alone is not enough. Adjustment of pH is made with the intention of promoting optimum activity of the amylase enzymes to hydrolyze mainly starch granules. According to application MX/a/2013/000943, the selected enzymes are of the amylase group of fungal origin with an optimum activity at pH value between 4 and 6 and temperatures from 50 to 80° C. In the present invention, after a thorough selection it was found that a certain type of amylase enzymes, preferably of bacterial origin can effectively perform at pH values between 6 and 8 and temperatures between 80 and 100° C., a feature that by itself already represents an advantage since no cooling of nejayote is needed. Additionally, it was found that at pH values between 7 and 10, the formation of floccules of the remaining suspended solid particles is very effective and no adjustment of ionic strength is needed, as it happens when the pH range is between 4 and 6; this way only sulphuric acid may be needed, that is much cheaper than phosphoric acid or any of its salts. However, due to regulatory requirements, and especially if the water to be recovered is going to be reused in the nixtamalization process, the method of the present invention also comprehends the use of phosphoric acid, its salts or citric acid in substitution of sulphuric acid. Even though these acids are more expensive than sulphuric acid, with the newly developed method, the adjustment of pH to only close values to neutrality implies a less expense of acids than it is when the pH to adjust is between 4 or 5, as described in application MX/a/2013/000943. Regarding phosphoric acid or its salts the savings are way greater since it forms buffer solutions, being one of the most stable ones the one it forms at its second pKa value of 7.2. The consumption of phosphoric acid to lower the pH of nejayote to that value is less than a third of that required to reach values between 4 and 5. In addition to cost reduction, an important advantage of the developed method is the physical characteristics of the floccules. Under the condition of the present invention, the formed floccules with the addition of sulphuric acid are very dense and compact, which facilitates greatly the separation process of the flocculated material, which, once sedimented, it usually does not represent more than 5% of the total volume treated. However, according to the method described in application MX/a/2013/000943, that volume tends to be superior to 50%, which requires sedimentation times much more prolonged or the use of equipment more sophisticated to achieve a satisfactory removal rate. The use of $CO_2$ gas currents resulting from the nixtamalization process to neutralize the pH of nejayote is possible, although a considerable amount of insoluble calcium carbonate is formed, which makes the organic suspended solid particles be substituted by those of inorganic nature. That means that the addition of other flocculants such as alumina is needed to improve the clarification of nejayote.

According to the objective of the present invention, a fundamental aspect of working at slightly alkaline pH values is referred with the technical operability or feasibility of the global process, particularly related to the use of ultra and/or nanofiltration and/or reverse osmosis membranes. The filtration elements of these membranes in any of their conformations are mostly made of polyamide, polymers of polysulphone and polyetersulphone, materials that according to their technical specifications are not compatible with surfactants or cationic flocculants positively charged, since these can cause irreparable damage to the membranes. At alkaline pH, the cationic flocculants are not positively charged and hence the risk of damage to the membranes is minimized. However, and with the purpose of eliminating all risk, it was also found in the present invention that another type of flocculants, like some kind of clay present in minerals of the phylosilicate group or the family of the smectites with other ingredients can substitute the cationic surfactants completely. Another relevant aspect which has to do also with the technical operability or feasibility of the system is that in acidic conditions the phenolic fraction of the nejayote is slowly adsorbed in the ultra and/or nanofiltration membranes, which causes its clotting and the reduction of the interest material. Probably, the phenolic compounds are positively charged in acidic conditions, like the cationic flocculants, causing the interaction or even chemical reaction with the membrane's materials.

To an expert in the art of the technique, it is evident that the method so far described can be developed both in batch and continuous systems. For a batch system, steps 1, 2, 3, 4 and 5 can be done in one vessel with either mechanical or pneumatic stirring and with a conical bottom to facilitate the draining of the flocculated suspended solid particles. In a semicontinuous system, steps 1, 2 and 3 can be done in a vessel similar to the batch system, but the addition of the flocculant (step 4) can be done in-line and the phase separation (step 5) can be done in a continuous machine. For example, a hydrosedimenter, a filter, a centrifuge or a flotation system can be used, taking care that the hydraulic residence time in the system is the necessary to achieve efficient flocculation and isolation. Finally, in a continuous system, pH adjustment can be done in-line, as well as the enzyme addition using a pass vessel with a continuous regime of charge-discharge and a volume in which the hydraulic residence time to achieve hydrolysis of the interest material is obtained. Instead of the vessel, a tubular piston reactor can also be used, or its equivalent, which would be a very long pipe in a compact arrangement but with enough steps to reach the hydraulic residence time needed to hydrolyze the material of interest. Then, the addition of flocculants can also be done in-line and the isolation of phases in the equipment already described for a semicontinuous system. It is also evident to someone experienced in the art of the technique that any of the operation regimes can be coupled with any instruments and automated to any desired level.

Having described the method for the elimination of suspended solid particles, it is next described the treatment system in one of its preferred modalities according to FIG. 2. Current 12 with a content inferior to 50 ppm of suspended solid particles enters a system of microfiltration MF, in any of its conformations, which has as objective to remove the rest of the suspended material. The resultant effluent, free of suspended solid particles, corresponds to current 14 in FIG. 2, and usually contains between 8000 and 17000 ppm of soluble compounds. Said current is then sent to vessel TA-C that serves as a balancing tank or feeding of the next element of the system. This next element consist of an ultrafiltration unit UF-100 with 100 kDa membranes of effective molecular weight cut. After evaluating membranes of different cut size, 100 kDa membranes retain a fraction of long-chain carbohydrates mainly composed of arabinose, xylose and ferulic acid, reason for which these substances are also known as ferulated arabinoxylanes or ferulated pentosans, since they have 5 carbon atoms and non-hydrolyzed ferulic acid molecules or p-coumaric acid. It was found that precisely these long-chain carbohydrates contribute to nejayote's thickness. From the element UF-100 two currents come out: a) the permeate or product described in FIG. 2 as current 16 that is sent to vessel TA-D, which serves as balancing tank or feeding to the next element; and b) the rejection described in FIG. 2 as current 18, which is concentrated by sending it as recirculation to vessel TA-C. While it is getting concentrated, viscosity of current 18 is greatly increased, which also means a considerable decline of current 16's flow. Both the increase in viscosity and the decline of the flow suggest a hyperbolic-type function. It was determined that it is possible to concentrate current 18 from 10 to 20 times, depending on the content of ferulated pentosans of current 14. Usually after concentration, current 18 has between 18000 to 22000 ppm of ferulated pentosans and low molecular weight compounds, while current 16 has between 7000 and 15000 ppm of soluble solids, which represents a reduction in its content of approximately 10 to 20%. Likewise, a COD of that current goes down to values between 5000 and 12000 mg $O_2$/L.

The separation of this first fraction of carbohydrates is important for technical and commercial reasons. The technical importance lies in that this fraction is the one that contributes greatly to the thickness of nejayote, which complicates the downstream processes. Commercially, ferulated pentosans have a market value due to their use in different fields, like the pharmaceutical industry, food industry or as a source of sugars for production of xilitol, bioethanol, unicellular protein or other biotechnology processes. If the purpose is the obtention of ferulated pentosans to be commercialized as an intermediate product, alternatively membranes of 50 kDa of effective cut may be used, with the intention of recovering a higher quantity of ferulated pentosans, although with a higher heterogeneity in the chain length. Additionally, current 18 needs to be diafiltrated with the purpose of permeating every compound with a lower molecular weight than 50 to 100 kDa retained by equilibrium effects. For diafiltration, the feed of unity UF-100 with current 14 must be interrupted momentarily, and instead feed vessel TA-C with current 14A of slightly alkaline water at pH values between 7.1 and 7.3, adding the permeate to current 16. It is advisable to diafiltrate with at least double the water volume present in vessel TA-C when diafiltration is started. Then, the resulting product of diafiltration, represented in FIG. 2, as current 18A, which contains between 15000 and 20000 ppm of ferulated pentosans of high purity is dried or purified by the already described processes. For example, current 18A can be directly dried by aspersion, atomization or sprayed, known also as spray dryers. Likewise, pure ferulated pentosans can be precipitated with ethanol and dried with acetone, as described in patent MX 278768. However, unlike the procedure described in that patent, the first product has been already purified and contains 10 to 20 times more ferulated pentosans of high molecular weight than nejayote. To precipitate these carbohydrates, addition of at least double the volume of ethanol is recommended, so working with a concentrated purified product represents savings from 10 to 20 times in the use of ethanol, acetone and the costs related to recovery and purification of these solvents. It is maintained that current 18A has a purified product because it is a current that has already gone through a process of hydrolysis with amylases and it has been diafiltrated, hence it is free of starch or carbohydrates of low molecular weight such as dextrins, pentose oligomers or monomers of glucose, xylose, arabinose, galactose, ferulic acid and other molecules. An additional advantage is that the ferulated pentosans present in current 18A are much more homogeneous regarding their molecular weight than the ones obtained in the procedure described in patent MX 278768, since ultrafiltration allows them to be separated from the carbohydrates of a lower molecular weight than 100 kDa of effective cut. Having a product more homogeneous in molecular weight is also directly correlated to the homogeneity of the physicochemical properties of the products to be developed or their respective application, for example as a gelling agent.

It will be obvious to someone skilled in the art that membranes of lower effective cuts are also useful to retain this fraction of carbohydrates but the fluxes (flow by membrane area unit) are slower, so a greater number of filtration units will be needed. Furthermore, homogeneity of the molecular weight of the ferulated pentosans will be smaller when molecules of intermediate size are also trapped, which will affect negatively the quality of the final product, or long chain ferulated pentosans, since they are the ones that have the greater number of applications because of their physicochemical properties in their solutions.

It will be also implicitly understood to the experienced in the art that the fractions of long chains pentosans will be able to be hydrolyzed chemically or enzimatically and thus avoid the ultrafiltration step. This, however, will not be the most attractive approach since these compounds are of high value.

After the first step of ultrafiltration, the resulting permeate represented in FIG. 2 as current 16, is sent to the vessel TA-D which serves as balancing or feeding to the next element of the system. This element is formed by unity NF-1 with nanofiltration membranes of 1 kDa of effective cut and from which two currents leave: a) the permeate or product described in FIG. 2 as current 20 which is sent to vessel TA-E that serves as balancing tank or feeding of the next element and b) the rejection described in FIG. 2 as current 22, which is concentrated and sent as recirculation to tank TA-D. Unlike current 18, the thickness of current 22 does not change substantially, only a slight decrease in flow is observed, which also describes, a lineal function that is proportional to the increase of the concentration of soluble compounds. It has been determined that it is possible to concentrate current 22 between 15 and 20 times, depending on the content of soluble solids of current 16. After concentration, current 22 usually contains between 16000 and 21000 ppm of ferulated pentosans with medium and low molecular weight, dextrins or arabinose, xylose and other sugars oligomers. Meanwhile, current 20 contains between 6000 and 12000 ppm of soluble particles, which represent a decrease in its content of approximately 10 to 20%. In the same way, COD of said current decreases to values between 4000 and 9000 mg $O_2$/L. Our studies also showed that nanofiltration membranes of 1 kDa of effective cut can be replaced by ultrafiltration membranes of 3 kDa or even 5 kDa, without substantially modifying the composition and contents of soluble solids of this second fraction. The decision to use membranes of 1, 3 or 5 kDa lies principally in their availability and specially their price, since the cost of replacement after its useful life, usually between one and three years, constitutes one of the operation costs of the process.

Separation of this second fraction of carbohydrates is also important for both technical and commercial reasons, since it contains compounds that impact the processes downstream, but that also can be used to obtain other products. According to our studies developed with the object of this application, this fraction is formed by pentosans of intermediate molecular weight, xylose and arabinose oligomers, dextrins, carbohydrates esters of medium or short chain with phenolic compounds, like ferulic acid, its dimmers or p-coumaric acid and other compounds of low molecular weight. The technical importance is that this fraction of carbohydrates is not completely hydrolyzed and can be separated from the following fraction formed by sugar monomers or dimmers. This way, the quantity of dissolved solids in the permeate or effluent of this operation, represented in FIG. 2 as current 20, is low, thus it facilitates the flow through the third element of nanofiltration or reverse osmosis, described below. One other advantage lies in the fact that said current 20, after going through the third element of nanofiltration or revers osmosis, can be concentrated in bigger proportion without the possibility of precipitation by an excessive concentration of compounds. This allows for a greater percentage of water recovered to be reused or discharged environmentally safely, and a bigger concentration of material that can serve for different biotechnological processes. Another aspect to stand out is that, as previously mentioned, this fraction contains ferulic acid or its dimers or trimers with pentose chains of intermediate or short chains, that according to our studies, are the ones that confer the characteristic brown color to the alkaline solutions that contain them. It was observed that these esters are also adsorbed during the recovery processes of ferulic acid, as the one described in patent MX 259521, which interferes in the processes of recovery and purification of ferulic acid, hence they are considered as contaminants of said process. Therefore, since the permeate or current 20 is free from that material and also from long chain ferulated pentosans retained in the ultrafiltration module UF-100, it is considered an ideal product to be used as raw material in the mentioned process for the recovery of ferulic acid. Additionally, it is mostly free of salts that may compete for active sites when the processes use adsorption resins, which enhances the process efficiency. Furthermore, esters of ferulic acid or their dimers or trimers that have been retained and concentrated in current 22 can be later treated with the use of enzymes of the feruloiesterase type, or chemically with the intention of promoting the liberation of a high-value molecule, such as ferulic acid, for its later recovery with already known processes. These molecules can also be used as nutraceuticals because of the multiple biological activities that they possess, as it is described in the electronic publication about short length arabinoxylanes coming from rice bran (http://www.biobran.org/overview/). They can also be used as prebiotics, since it has been described that hemicellulose, formed by pentoses, beneficially affects the host by selectively stimulating the growth and/or activity of one or a limited number of colon bacteria. In another application, these carbohydrates can be either chemically or enzymatically digested along with the dextrins or glucose oligomers, which form this second fraction, with the intention of using its sugars for the production of bioethanol or as a substrate for different biotechnological processes.

The second fraction may or may not be diafiltrated, depending on the use this fraction or permeate is intended for. If recovery of high value molecules, like free ferulic acid, is intended, the diafiltration is necessary. If short chain or intermediate chain pentosans are pretended to be isolated and purified to be used as nutraceutical or prebiotics, a previous enzymatic or chemical digestion of dextrines or glucose oligomers is needed. For the diafiltration of this second fraction, feeding of unity NF-1 with current 16 must be momentarily interrupted, and instead the vessel TA-D must be fed with current 16A of slightly alkaline water at pH values between 7.1 and 7.3, while incorporating the permeate to current 20. It is advisable to diafiltrate with at least twice the volume of water present in vessel TA-D when it starts. Then, the resulting product of diafiltration, represented in FIG. 2 as current 22A, which contains from 14000 to 19000 ppm of short-chain or medium-chain pentosans, its esters with ferulic acid or its dimers or trimers; can be treated according to the user's requirements. Current 22A may or may not contain dextrins or glucose oligomers depending on whether an enzymatic hydrolysis with dextrinase and/or glucosidase-type enzymes is applied previous to the diafiltration, where glucose monomers or dimers are eliminated.

After going through the first element of nanofiltration (second of the system), the resulting permeate represented in FIG. 2 as current 20, is sent to vessel TA-E which serves as a balancing tank or feeding to the third element of the system. This element is composed by the unity NF-02 with nanofiltration membranes of 200 Da of effective cut and from which two currents come out: a) the permeate or product described in FIG. 2 as current 24, which is sent to vessel TA-F that serves as balancing tank or feeding to the next element of the system or as water storage to be reused in the nixtamalization process or its posterior discharge in an environmentally safe way; and b) the material rejected, described in FIG. 2 as current 26, which is concentrated by sending it as recirculation to vessel TA-E. Like current 22, the thickness of current 26 does not change significantly and only a small decrease in flow is perceived, which also presents a lineal function proportional to the increase of the concentration of soluble particles. It has been determined that current 26 can be concentrated between 6 and 12 times, depending of the content of soluble particles of current 20. Usually, after concentration, current 26 contains from 20000 to 55000 ppm of different sugars, free ferulic acid and dimers of ferulic acid principally. This current, rich with high value compounds like ferulic acid and its derivatives, is ideal to be used in processes that intend its recovery, since it is moistly already free of material that interferes in said processes like short-chain, intermediate-chain and long-chain arabinoxylans bonded to ferulic acid molecules, its dimers and trimers. By being concentrated, this fraction will also reduce the treatment time with the consequent cost reduction of man- and energy-hours. For its part, current 24 contains between 1000 and 2200 ppm of soluble particles, of which approximately 40% are inorganic salts, which represents a reduction in their content of about 75 to 85%. COD of current 24 shows a substantial reduction, by presenting values of between 400 to 1000 mg $O_2$/L and conforms water with acceptable quality, free of phenolic compounds that may degrade and confer unwanted organoleptic properties to the final product, reason for which it can be recirculated again in the nixtamalization process.

If the intention is to discharge current 24 in an environmentally safe way, membranes of the element NF-02 can be replaced by membranes of 100 Da of effective molecular weight cut, or by reverse osmosis membranes. It will be obvious to a skilled in the art that with the purpose of optimizing the system's functionality, in other setting of the system, the 100 Da membranes or the reverse osmosis membranes may be set sequentially as a fourth element where current 24 is the influent. With the 100 Da or the reverse osmosis membranes permeates with a lower content of soluble particles than 300 ppm and COD values lower than 200 mg $O_2$/L are obtained; which is under the maximum limits established by most of the environmental laws for this parameter.

The fractioning of the components of nejayote so far described, plus the commercial component of isolating them in three different valuable fractions, has as a technical purpose to optimize the functioning of the membranes. According to our studies, it was observed that when only one membrane of low molecular weight effective cut, such as 200 Da, is used; pore saturation is almost immediate and it provokes a very slow flow. Furthermore, as the effluent concentrates, solid suspended particles begin to form, point in which the operation must be interrupted. This state is reached when the influent has been concentrated barely from 3 to 5 times.

In another modality of the present invention, currents 14, 16 or 26 that contain free ferulic acid, can be subjected to an additional treatment with the intention of removing other more complex phenolic compounds, such as lignin, that usually interfere in the processes of recovery of ferulic acid, like the one described in patent MX 259521. The method consists in lowering the pH to values under 4.5, from which new suspended particles begin to form, specifically by the complex phenolic compounds and, since they are acidic substances with pKa under 5, the equilibrium point is displaced to their molecular form, insoluble in water. It was found that the greatest formation of these insoluble species happens at pH values under 3.5, to the point of forming stable suspensions or emulsions which are hard to separate by conventional unit operations like decanting, microfiltration or centrifugation. We found that the addition of certain type of clay that contain minerals of the group of phyllosilicates or the family of smectites and other ingredients favour the flocculation of the new suspended particles, or micelles that form the emulsions. The optimum amount to reach of the clay mix is from 200 to 2000 ppm, preferably from 500 to 800 ppm, added as powder and keeping the stirring of the heterogenous mix from 5 to 25 minutes, preferably from 10 to 20 minutes until achieving an efficient flocculation of the suspended material. This operation is more efficient if the temperature is kept between 40 and 70° C. The flocculated material can then be removed by conventional unit operations, like decanting, sedimentation, centrifugation, filtration, flotation or any combination of them.

It will be evident to the skilled in the art, that in other less desired method, the concentrated fractions formed by currents 18, 22 and 26 can be mixed and treated by conventional aerobic/anaerobic methods, although it should be in much smaller volumes since the add-up of the three subfractions represents on itself between 15 and 25% of the total nejayote volume to be treated.

EXAMPLES OF THE INVENTION

The invention will now be described according to the following examples, which are stated only with the purpose of representing a way of implementing the principles of the invention. The following examples are not an exhaustive representation of the invention, or try to limit its scope.

Example 1

Glass beakers with 500 mL of nejayote were prepared, with an initial pH value of 12 that was immediately adjusted to the pH value required for each of the treatments. Five treatments and an absolute control were applied, and after 30 minutes, the following response variables were measured: total suspended solid particles (TSS) in the supernatants, volume of the precipitated flocs (V) and the maximum volume (Vmax) that can be filtrated in 15 minutes through a 0.45 mm-cut, 4.5 cm-diameter nitrocellulose membrane, and applying vacuum of 400 mbar. Treatment 1 corresponds to the method described in patent application MX/a/2013/000943 using phosphoric acid, an amylase of fungal origin and a polyacrylamide flocculant. Treatment 2 corresponds to a modality of the method of the present invention, using sulphuric acid, an amylase of bacterial origin and clay as flocculant. Treatment 4 corresponds to a modality of the method of the present invention, using citric acid, an amylase of bacterial origin and polyacrylamide as flocculant. Treatment 5 corresponds to a modality of the present invention, using $CO_2$, an amylase of bacterian origin and polyacrylamide as flocculant.

Except for treatment 5, the removal of the suspended solid particles by any of the other treatments was superior to 97%, and the acid spending was at least 9 times lower in treatments 2 and 3 when compared to treatment 1. The flocculated solids were 5 times more compact (lower volume or higher density) when compared to those obtained with treatment 1.

|  | Control | Treat. 1 | Treat. 2 | Treat. 3 | Treat. 4 | Treat. 5 |
|---|---|---|---|---|---|---|
| Flocculant (ppm) | — | 17 | 17 | 500 | 17 | 17 |
| Enzyme (μL) | — | 50 | 50 | 50 | 50 | 50 |
| $T_0$ (° C.) | 65 | 65 | 65 | 65 | 65 | 65 |
| $T_F$ (° C.) | 55 | 55 | 55 | 55 | 55 | 55 |
| $pH_0$ | 12 | 12 | 12 | 12 | 12 | 12 |
| $pH_F$ | 11 | 5.0 | 7.2 | 7.2 | 7.2 | 7.2 |
| Added acid (mL) | — | 2.2 | 0.8 | 0.8 | 0.8 | NA |
| Acid cost ($USD/m$^3$) | — | 5.3 | 0.6 | 0.6 | 1.8 | — |
| TSS (ppm) | 920 | 23 | 18 | 27 | 31 | 368 |
| V (mL) | <50 | 210 | 47 | 56 | 61 | 59 |
| Vmax (mL) | <50 | 250 | 240 | 210 | 190 | 105 |

The cost of enzymes of fungal or bacterial origin is somewhat similar, while the cost of clay, although is higher to that of the polyacrylamide flocculant, does not represent more than 20% of the total cost of the treatment, due to the amount needed.

Example 2

In order to evaluate the effect of the methods of total suspended solid particles (TSS) of nejayote over the percentage of recovery of material in the different steps of ultra/nanofiltration used in the system, 2 L aliquots of SST-free nejayote were used, which were obtained by two methods: 1) the method described in application MX/a/2013/000943 (acidic conditions, pH 5.0) and 2) method described in the present invention (alkaline conditions, pH 7.2). The matter balancing was done considering the content of the soluble solids of membrane influents, the permeates, filtration rejections and the volumes of each of them.

|  | Matter Balancing (% of recovery) | |
|---|---|---|
| Membrane | Acidic contitions | Alkaline conditions |
| 30 KDa | 90 | 96 |
| 5 KDa | 75 | 95 |
| 1 KDa | 70 | 100 |

With the membranes of lower effective molecular cut, the percentage of matter recovery was inferior to 76%, showing a high retention of the soluble solids in the membranes' materials, possibly from physical or chemical adsorption.

Example 3

Clarification
Nejayote volume=10 L
Material in solution=11.7 g/L
Phenolic compounds in solution=1.2 g/L
Suspended materials=2250 ppm
Nejayote adjusted pH value=7.3
Nejayote initial temperature=72° C.
Volume of bacterial amylases added=1 mL
Incubation time=10 min
Final content of polyacrylamide flocculant=20 ppm
Suspended solid particles in clarified nejayote=21 ppm
Sludge volumen in hydrosedimenter=350 mL
Content of solid in sludge=64 g/L
Microfiltration
Q=10 L/h
Filtrating area=95 cm$^2$; 20-25 μm pore
Suspended solid particles in clarified/filtrated nejayote=2 ppm
Solid particles in solution in clarified/filtrated nejayote=9.5 g/L
Phenolic compounds in solution=1.2 g/L
Ultrafiltration
Molecular weight effective cut=100 KDa; area=929 cm$^2$
Permeate=95% of Q=1.8 L/h, containing 8.5 g/L de soluble solids, of which 12% are free and glycosylated phenolic compounds, 14% of carbohydrates containing glucose, 7% of carbohydrates containing xylose and arabinose, 39% ashes and the rest carbohydrates containing unquantified sugars like galactose or manose. Concentrate=5% of Q=1.8 L/h, containing 24 g/L of soluble solids, formed by 65% of long chain ferulated arabinoxylans, 16% ashes y 6% of glucose-containing carbohydrates. Composition of the concentrate after diafiltration in a 50 KDa membrane was 80% of long chain ferulated arabinoxylans and 5% ashes. Galactose and manose of the ferulated arabinoxylans was not quantified.
Nanofiltration 1
Molecular weight effective cut=1 KDa; area=5574 cm$^2$
Permeate=95% of Q=6.6 L/h, containing 7.7 g/L of soluble solids, of which 13% are phenolic compounds, 42% ashes y 14% glucose.

Concentrate=5% of Q=6.6 L/h, containing 18 g/L of soluble solids, formed by 55% of ferulated arabinoxylanes of intermediate and/or short chain 18% ashes y 12% of glucose oligomers.

Nanofiltration 2

Molecular weight effective cut.=200 Da; area=76 ft$^2$

Permeate=85% of Q=220 L/h, containing 1.1 g/L of soluble solids, of which 9% are phenolic compounds, 45% ashes, 9% glucose and other unidentified carbohydrates of low molecular weight; COD=427 mg O$_2$/L; BOD=290 mg O$_2$/L. Concentrate=15% of Q=220 L/h, containing 45 g/L de soluble solids, formed by 13% of phenolic compounds, 42% ashes, 12% of glucose and other unidentified carbohydrates of low molecular weight.

Reverse Osmosis as Alternative to Nanofiltration 2

Area=76 ft$^2$

Permeate=80% of Q=180 L/h, containing 0.08 g/L de soluble solids, of which 10% are phenolic compounds, 39% ashes, 10% glucose and other unidentified carbohydrates of low molecular weight; COD=54 mg O$_2$/L; BOD=25 mg O$_2$/L. Concentrate=20% of Q=180 L/h, containing 38 g/L of soluble solids, formed by 12% of fenolic compounds, 42% ashes, 12% glucose and other unidentified carbohydrates of low molecular weight.

Example 4

The recovery of phenolic compounds from current 14 (M14), current 20 (M20) and a supernatant obtained after removing the total suspended solid particles was compared using the method described in application MX/a/2013/000943 (MpH5). One aliquot of 1 L of each was taken and the pH value of M14 and M20 was adjusted to 5. Then, the three samples were added 30 g of cationic resins to adsorb the soluble phenolic compounds, with constant stirring in an orbital agitator at 150 rpm for 6 hours, until equilibrium was achieved. After that period, the supernatants were draines and the resins were washed with distilled water, and once drained they were eluted with three aliquots of alcohol at 95% (v/v). The three elution aliquots were mixed together, concentrated in a rotary evaporator to reach 30 mL and evaporated to dryness under an air current. The recovered material was quantified by gravimetric analysis. In all cases the phenolic compounds were spectrophotometrically quantified at 320 nm over a standard curve of ferulic acid.

|  | M14 | M20 | MpH5 |
| --- | --- | --- | --- |
| Suspended solid particles (ppm) | 15 | 0 | 22 |
| Soluble solid particles (g/L) | 10.2 | 7.6 | 10.4 |
| Initial pH value | 7.2 | 7.2 | 5.0 |
| Initial phenolic compounds (g/L) | 1.1 | 0.9 | 1.1 |
| Adjusted pH value | 5.0 | 5.0 | 5.0 |
| Ethanolic solid eluted residue (g) | 1.2 | 0.8 | 1.3 |
| Crystal presence | − | +++ | − |
| Ethanolic residue color | Café | amarillo | café |

It was observed in the phenolic fraction from M20 that a considerable amount of aggregated crystals was formed in some points of the petri dish where the eluted concentrated ethanolic solution was evaporated. Likewise, the color of the rest of the uncrystallized material was between yellow and light brown, and it was identified as a thin layer deposited in some parts of the walls and bottom of the container. On the other hand, in the material from M14 and MpH5 there were no crystals, and the thin layer deposited in the bottom and walls of the container was dark brown. The present example is a clear representation of the effect of removing some fractions of nejayote, through the system of ultrafiltration membranes of different molecular cut, about the crystallization of ferulic acid.

Example 5

The suspended solid particles were removed applying the method described in application MX/a/2013/000943, obtaining a clarified nejayote (CN1) and with the method objective of the present invention, described in example 1, obtaining a clarified nejayote (CN2). They each were divided in two aliquots of 1 L. The first aliquot of CN1 was maintained with no change at a pH value of 5, and corresponds to sample CN1A. Then, the first aliquot of CN2 was adjusted to a pH value of 5 and corresponds to sample CN2A. The other two aliquots were adjusted to a pH value of 3, and it was observed that from pH 4.5, the initially translucent solutions began to turn opaque until a milk-like emulsion was formed at pH 3. Each aliquot was added 500 mg of clay containing minerals of the family of smectites and was kept in stirring for 5 minutes, after which the formed flocs were isolated by decanting and the supernatant was filtrated with whatman paper 4. The supernatant free of flocs from CN1 corresponds to sample CN1B of this example, whilst supernatant from CN2 corresponds to sample CN2B. 30 g of cationic resins were added to all 4 samples do adsorb the soluble phenolic compounds, while stirring in an orbital shaker at 150 rpm for 6 hours to reach equilibrium. After that period, the supernatants were drained and the resins were washed with distilled water. Once they were drained, resins were eluted with three 100 mL aliquots and alcohol at 95% (v/v). All three eluted aliquots were mixed together and concentrated to reach approximately 100 g/L of phenolic compounds. In all the cases the phenolic compounds were spectrophotometically quantified at 320 nm over a standard curve of ferulic acid. The concentrated solutions were poured on distilled water, evaporating ethanol with heating at 80° C. for 10 minutes; after which they were left to cool and left to settle for 24 hours. After that time the crystals deposited in the bottom of the containers were collected and, after using a hot air current to dry it, it quantified by gravimetry.

|  | NC1A | NC1B | NC2A | NC2B |
| --- | --- | --- | --- | --- |
| Suspended solid particles (ppm) | 12 | 12 | 8 | 8 |
| Soluble solid particles (g/L) | 9.0 | 9.0 | 9.6 | 9.6 |
| Initial pH | 5 | 5 | 7.2 | 7.2 |
| Initial phenolic contents (g/L) | 0.97 | 0.97 | 0.96 | 0.96 |
| Adjusted pH value | 5 | 3 | 5 | 3 |
| Suspended solids at adjusted pH (ppm) | 12 | 420 | 8 | 395 |
| floculation suspended solids (ppm) | 12 | 9 | 8 | 11 |
| Final phenolic compounds content (g/L) | 0.97 | [1]0.91 | 0.96 | [1]0.89 |
| Adsorption phenolic compounds (g/L) | <0.05 | <0.05 | <0.05 | <0.05 |
| Eluted etanol phenolic contents (g/L) | 3.2 | 3.0 | 3.1 | 2.9 |
| [2]Ferulic acid as crystals (g) | — | 0.3 | 0.1 | 0.4 |

[1]After acidification of supernatant at a pH value of 3, floclate with clay and separate the formed flocs.
[2]Includes only the materials forming sharp-pointed crystals or mycrocristals (as seen under the microscope).

Crystal formation was not observed in the phenolic fraction of CN1A, rather an emulsion was formed initially which after 24 hours was broken when a thin brown layer containing the phenolic fraction was settled in the bottom and walls of the container. A small quantity of crystals was observed at the bottom, that once separated and dried were of a more intense yellow color (less pure) than those of sample CN2B. This example is a clear representation of the effect of removing undesirable phenolic compounds by a method of acidification at a pH value of 3 and flocculation of the new insoluble material with the use of clay, over the crystallization of ferulic acid.

After reading and understanding the detailed description preceding a method and system, in the preferred modalities of the invention for the treatment of effluents of the nixtamalization processes, commonly known as nejayote, several advantages that offer said method and system will be perceived for the objective they were created.

Without the intention of expressing every relevant aspects of the invention, the following advantages can be pointed:

the combination of an improved method for the removal of suspended solides in nejayote and an adequate filtration system for the separation and concentration of its soluble fractions form an integral process that not only enables the treatment of an industrial effluent but also originates a series of compounds with commercial value. This feature gives the present invention positive impacts in the technological, economic, social and environmental fields. So far, the highly contaminant effluents that result from the process of corn nixtamalization had not been able to be efficiently treated by conventional methods or other technologies.

the integral process is the result of thorough studies to establish the ideal conditions to make operable the global process as: 1) pH value that allows, on the one hand, an efficient removal of the suspended solid particles, and on the other hand, avoids the adsorption or retention of compounds like fats, oil, phenolic compounds and flocculants in the material of the ultrafiltration, nanofiltration or reverse osmosis of membranes; 2) use of cationic flocculants in alkaline conditions or use of other flocculants like some kind of clays with the purpose of avoiding any chemical damage in the membranes; 3) selection of membranes with molecular weight effective cuts, in a way in which concentrated currents with fractions and effluents of interest are generated that allow the performance of the subsequent processes in cascade, which conform the present invention. The operation with membranes of a single pore size causdes a fast clotting, decreasing their fluxes and reducing ther concentration capability. An higher amount of soluble solids in a single fraction reach quickly the saturation point, which causes again the creation of suspended solid particles.

Some currents are generated which can be used advantageously in the processes already described, that are intended to recover compounds of high value, like ferulated pentosans and ferulic acid. Even in one of the modalities, the present invention includes a method to remove unwanted phenolic compounds that interfere with the known processes for the recovery and purification of ferulic acid from the effluents of the nixtamalization of corn.

Based on the previously described realizations, it is contemplated that the modifications of the described realizations or their configurations, as well as the alternate realizations or their configurations will be considered evident to a person skilled in the art of the technique under the present description. It is hence contemplated that the claims cover said modifications and alternatives that are within the scope of the present invention or their equivalents.

The invention claimed is:

1. A continuous, semicontinuous or batch process for the treatment of the effluent of the process of nixtamalization commonly known as nejayote, which comprises the steps of:
    (a) eliminating or removing suspended solid particles through a method of enzymatic hydrolysis and flocculation,
    (b) filtering the nejayote through a microfiltration system to remove the remaining suspended solid particles from step (a) and,
    (c) filtering the micro-filtered nejayote, resulting from step (b), through an ultrafiltration membrane system of ≤100 kDa of molecular weight cut off in order to separate it into a first permeate current and a first concentrate current, wherein the first permeate current contains water, salts and soluble solid particles of intermediate and low molecular weights ≤100 kDa, and wherein the first concentrate current contains water and soluble solid particles of high molecular weights >100 kDa, and,
    (d) filtering the first permeate current from step (c), through a nanofiltration membrane system of ≤1000 Da of molecular weight cut off in order to separate it into a second permeate current and a second concentrate current, wherein the second permeate current contains water, salts and soluble solid particles of low molecular weight <100 Da, and wherein the second concentrate current contains water and soluble solid particles of intermediate molecular weights >100 Da and,
    (e) filtering the second permeate current from step (d), through a reverse osmosis membrane system in order to separate it into a third permeate current and a third concentrate current, wherein the third permeate current contains water, and wherein the third concentrate current contains water, salts and soluble solids of low molecular weights <100 Da.

2. The method according to claim 1, wherein the step (b) microfiltration step comprises a microfiltration system to retain remaining suspended solid particles, allowing no more than 2 ppm of total suspended solids (TSS) in the effluent.

3. The method according to claim 1, wherein the step (c) ultrafiltration step, comprises an ultrafiltration system including ultrafiltration membranes of 3, 5, 30, 50 or 100 kDa of molecular weight effective cut off.

4. The method according to claim 1, wherein the step (d) nanofiltration step, comprises a nanofiltration system including nanofiltration membranes of 100, 200 or 1000 Da of molecular weight effective cut off.

5. The method according to claim 1, wherein the first concentrate current, obtained from step (c), is characterized by a soluble solids content composed of ferulated arabinoxylans of long chain and ash.

6. The method according to claim 1, wherein the first permeate current obtained from step (c) is characterized by a soluble solids content composed of free and glycosylated phenolic compounds, carbohydrates containing glucose, arabinose and xylose of intermediate and short chains, free sugars and ash.

7. The method according to claim 1, wherein the second concentrate current, obtained from step (d) is characterized by a soluble solids content composed of glycosylated phenolic compounds, carbohydrates containing glucose, arabinose and xylose of intermediate chain and ash.

8. The method according to claim 1, wherein the second permeate current obtained from step (d) is characterized by a soluble solids content composed of free phenolic compounds, carbohydrates containing glucose, arabinose and xylose of short chain, free sugars and ash.

9. The method according to claim 1, wherein the third concentrate current obtained from step (e), is characterized by a soluble solids content composed of free phenolic compounds, carbohydrates containing glucose, arabinose and xylose of short chain, free sugars and ash.

10. The method according to claim 1, wherein step (a), comprises the steps of:
   (a1) adding acidic substance(s),
   (a2) adding amylase-type enzymes,
   (a3) incubating nejayote for a specific period of time,
   (a4) adding to hydrolyzed nejayote a flocculant; and
   (a5) isolating the flocculate material.

11. The method according to claim 10, in which step (a1) is characterized by the addition of acidic substance(s) to lower the pH to values between 6.5 and 8.0.

12. The method according to claim 10, wherein in step (a1) the acidic substance(s) is(are) selected from the group consisting of citric acid, sulphuric acid and phosphoric acid.

13. The method according to claim 10, wherein in step (a1) the acidic substance(s) is (are) added alone or as a mixture.

14. The method according to claim 10, wherein in step (a2), the amylase-type enzymes added, comprise amylases of bacterial origin with optimum pH activity values between 6.0 and 8.0.

15. The method according to claim 10, wherein in step (a2), the amylase-type enzymes are added in volumes between 10 to 200 uL per liter of nejayote, according to the specific activity of the amylase-type enzymes, the content of material to be hydrolyzed in nejayote and the desired time for hydrolysis.

16. The method according to claim 10, wherein in step (a3), the incubation time of the resulting mixture is from 1 minute to 60 minutes.

17. The method according to claim 10, wherein in step (a3), where the incubation temperature of the resulting mixture is from 50 to 100° C.

18. The method according to claim 10, wherein in step (a4), the added flocculant is selected from the group of polyacrylamides or from the group of clays containing minerals of the group of phyllosilicates or the family of smectites and other active compounds.

19. The method according to claim 10, wherein in step (a4), the polyacrylamide flocculants are added to reach a concentration between 5 to 100 ppm, and wherein the clays are added to reach a concentration between 200 and 2000 ppm.

20. The method according to claim 10, wherein in step (a4), the time needed to flocculate the suspended solid particles goes from 1 to 15 minutes.

21. The method according to claim 10, wherein in step (a5), the isolation of the flocculated material is done through the use of one of the following unit operations:
   sedimentation,
   decantation,
   filtration,
   centrifugation, or
   flotation.

* * * * *